US006328706B1

(12) United States Patent
Yattavong

(10) Patent No.: US 6,328,706 B1
(45) Date of Patent: Dec. 11, 2001

(54) WRIST SUPPORT DEVICE

(76) Inventor: Khamkong Yattavong, 188 Logan Avenue, Toronto Ontario (CA), M4M 2N3

( * ) Notice: Subject to any disclaimer, the term of this patent is extended or adjusted under 35 U.S.C. 154(b) by 0 days.

(21) Appl. No.: 09/562,856

(22) Filed: May 1, 2000

(51) Int. Cl.[7] .................................................. A61F 5/00
(52) U.S. Cl. ................................ 602/21; 128/878; 2/16
(58) Field of Search ................................. 128/846, 877, 128/878, 879; 602/20, 21, 22; 2/16, 160, 161.6, 162, 163; 473/61, 62, 63

(56) References Cited

U.S. PATENT DOCUMENTS

| 4,479,648 | * | 10/1984 | Alivo | 602/21 |
| 5,203,766 | * | 4/1993 | Carter | 602/21 |
| 5,413,120 | * | 5/1995 | Grant | 128/878 |
| 5,722,092 | * | 3/1998 | Borecki | 602/21 |

* cited by examiner

Primary Examiner—Michael A. Brown

(57) ABSTRACT

A wrist support device for allowing limited extension and flexion of the wrist but substantially limiting movement of the wrist in all other directions and further substantially limiting pressure from being placed on the wrist is disclosed. The wrist support device includes a first elongated channel shaped rigid member for aligning with the longitudinal axis of the user's forearm for abutting against the posterior aspect of the forearm and a second small rigid substantially flat member independent from the first member for aligning with the longitudinal axis of the user's forearm and abutting against the anterior aspect of the forearm. The two members are attached together and secured to the user's forearm by a plurality of releasable fastening members, such that when tightened, the wrist support device limits extension and flexion of the wrist and substantially limits pressure being placed on the wrist.

21 Claims, 8 Drawing Sheets

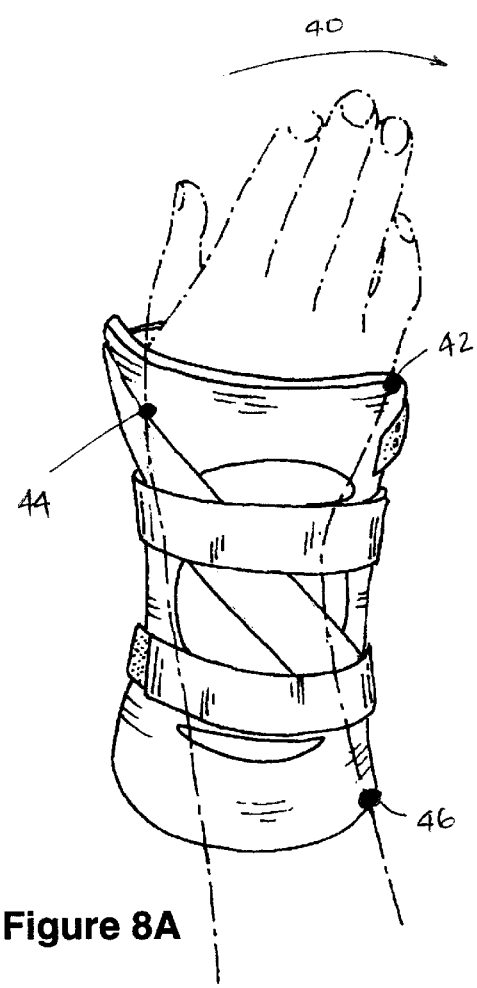
Figure 8A
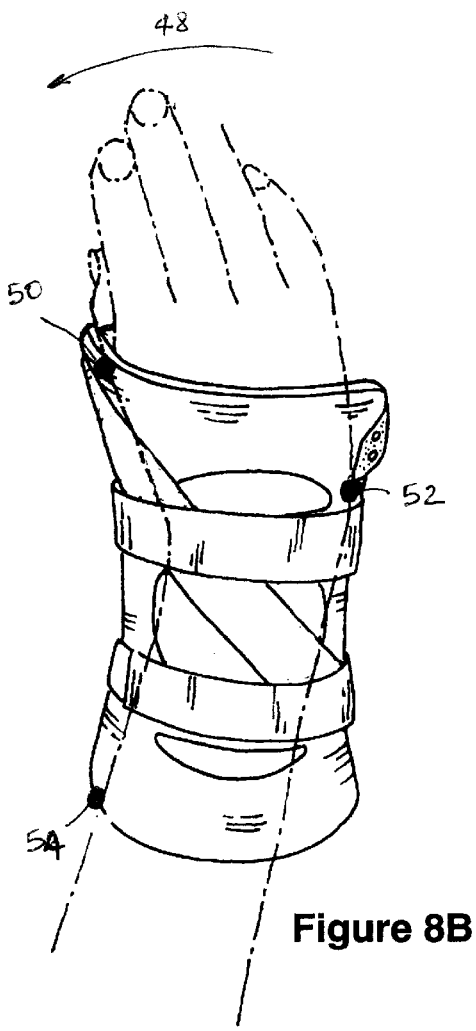
Figure 8B
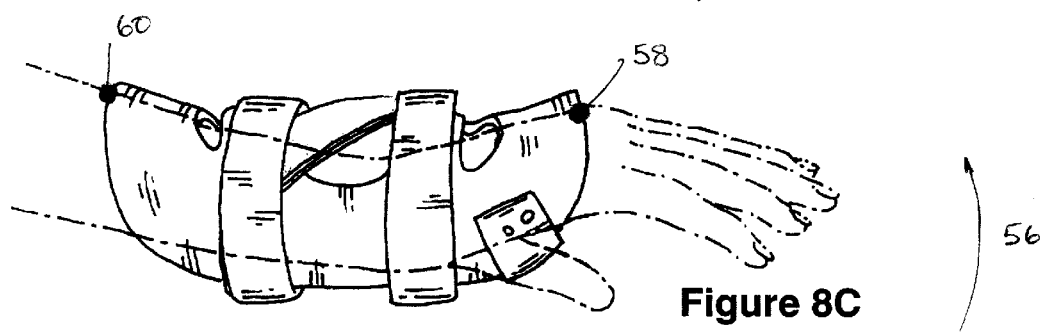
Figure 8C
Figure 8B
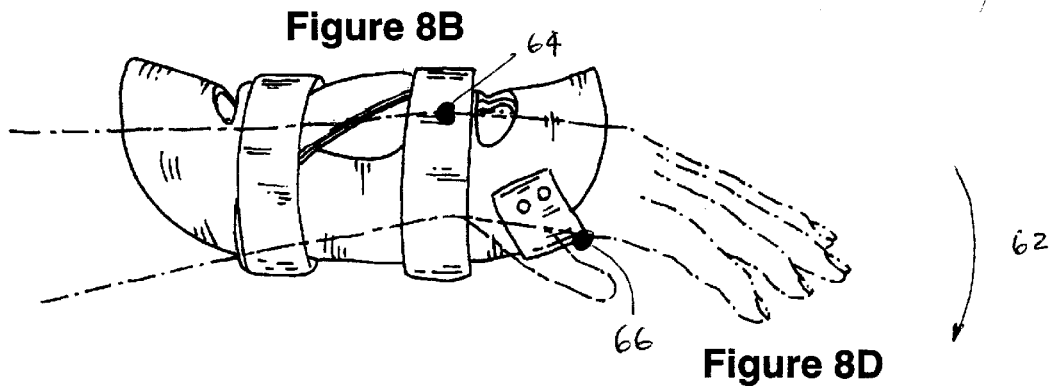
Figure 8D

WRIST SUPPORT DEVICE

FIELD OF THE INVENTION

The present invention relates to wrist supports and more particularly to a wrist support for extended daily wear to permit use of the hand by the wearer.

BACKGROUND OF THE INVENTION

Various types of wrist supporting devices that restrict movement of the wrist in one way or another are available for a variety of purposes. The motion(s) restricted and the way(s) in which way in this is achieved varies.

For example, a bowler's wrist brace is described in U.S. Pat. No. 4,479,648, which issued Oct. 30, 1984. This brace includes a rigid channel member custom fit for receipt of a wearer's forearm therein. The brace is designed for supporting a wearer's wrist when throwing a bowling ball and so endeavors to ensure that a predetermined angle between hand and wrist is maintained for a proper release of the ball from the bowler's hand.

In another example, U.S. Pat. No. 5,203,766, issued Apr. 20, 1993, describes a wrist brace which aids healing of a fracture of the lower end of the radius, known in the medical community as a "Colles fracture". The brace is intended to be worn by a person throughout the healing process and so is adjustable to permit the degree of restriction placed on the wearer's wrist to be varied, particularly pivotal movement of the wrist about the radiocarpal joint, depending upon the stage of repair of the person's wrist. To this end, the brace is composed of several parts. The desired fit is rather precise and use of an X-ray machine in fitting of the brace is described.

U.S. Pat. No. 5,722,092, issued Mar. 3, 1998, describes a protective arm and wrist guard for use by a sports participant, particularly a snowboarder. The guard comprises a substantially rigid dipartite sleeve adapted to receive the distal forearm, wrist and proximal portion of a hand; thumb receiving region at one end of the sleeve to receive and partially surround the base of the thumb of a user and retaining straps to hold the sleeve on the arm of a user.

SUMMARY OF THE INVENTION

An aspect of the present invention is to provide a wrist support device that can be worn throughout the day by a person who needs to use their hand, say a worker in the roofing industry for gripping and using a hammer. At the same time, the device provides support to immobilize the wearer's wrist, as described further below, so as to reduce damage to the wrist from repetitive hammering action, for example, and to reduce pain that may result from movement of the wrist due to prior injury.

The invention therefore provides for a wrist supporting device, which allows limited extension and flexion of the wrist but substantially limits movement of the wrist in all other directions and further substantially limits pressure from being placed on the wrist and comprises a first elongated channel shaped rigid member having a generally longitudinal axis for aligning with the longitudinal axis of a user's forearm and abutting against the posterior aspect of the forearm. The lateral and medial aspects of the member substantially surround the lateral and medial aspects of the user's forearm, the member extending from about the metacarpo-phalangeal joint of the user's hand to about the mid forearm. The term "lateral" as used herein refers to a structure being further away from the median plane than another structure in the body. The term "medial" as used herein refers to a structure being closer to the median plane than another structure in the body. The term "median" as used herein refers to the midline plane dividing the body into left/right halves. Preferably, the proximal and distal portions of the member curve upwards and outwards at about a 30° and 20° angle respectively, relative to the longitudinal axis. The terms "proximal" and "distal" are employed with reference to the limbs only. The term "proximal" as used herein refers to a structure being closer to the median plane or root of the limb than another structure in the limb. The term "distal" as used herein refers to a structure being further away from the median plane or root of the limb than another structure in the limb. The distal lateral or medial edge portion of the member further have an aperture for receiving a velcro strap, wherein one end of the velcro strap is fixedly attached to the distal portion of the member substantially opposite the aperture and the free end of the velcro strap is passed through the aperture for releasably attaching to the top surface of the member. The velcro strap spans the wearer's palm between the thumb and the index finger. It is preferable that the velcro strap comprise of leather. The device also comprises a second small rigid substantially flat member independent from the first member for aligning with the longitudinal axis of the user's forearm and abuts against the anterior aspect of the forearm. The second member extends from about the carpo-metacarpal joint of the user's hand to about the lower forearm. A plurality of releasably attaching fastening members are adapted to attach the first and second members together and secure the first and second members to the wearer's hand such that when the fastening members are tightened the second member abuts the anterior aspect of the user's arm and is positioned so as to extend from about the carpo-metacarpal joint of the user's hand to about the lower forearm thereby limiting extension and flexion of the wrist and substantially limiting pressure being placed on the wrist.

In another aspect of the invention, the wrist support device comprises vents for providing comfort to the wearer. It is important, however, that the vents not be positioned such that they correspond to the radiocarpal joint of the wearer.

In yet another aspect the invention, the wrist support device comprises cushioning means on the surface abutting the wearer's arm for providing comfort to the wearer.

In yet another aspect of the invention, the cushioning means of the first member in the region corresponding to the radiocarpal joint is wedged shape with the widest portion of the wedge facing distally and tapering in thickness towards the proximal, lateral and medial aspects of the member.

In a second embodiment, the invention calls for a wrist support to immobilize movement of the hand and forearm of a person with respect to each other about the wrist, the support comprising a tubular member comprising a wall of generally arcuate cross section, shaped to receive contiguous portions of a person's forearm, wrist and hand therein, wherein the member is dimensioned and is sufficiently flexible to permit radially inward flexure of the lengthwise sides of the member for fitting of the posterior and sides of the forearm, wrist and hand in abutment against an inner concave surface of the wall in use, and sufficiently rigid to preclude flexure of the wall in other directions; first and second flexible straps, wherein each strap is secured to the outer back of the wall and disposed to permit extension of the strap from a first to a second lengthwise edge of the tubular member, to span a gap between the edges, wherein there is an aperture defined adjacent the second edge to permit passage of the strap therethrough and looping of the strap back onto itself, to permit the radial inward flexure of the lengthwise sides of the member by drawing of the strap through the aperture; complementary hook and loop fasteners disposed on the outer back of the wall and the free end of each strap to permit the looped-back end of each strap to be secured in a position selected by the person in which the inner concave surface of the wall is in abutment with the posterior and sides of the forearm, wrist and hand; a rigid member having first and second openings therein for passage of the first and second straps therethrough to locate the rigid member in the gap, in use, in abutment with an anterior surface of the arm wherein each opening is dimensioned with respect to the strap passing therethrough such that the rigid member is substantially fixed against axial movement with respect to the tubular member when the straps are in a secured position; a distal first end of the tubular member is flared such that an inner surface portion thereof limits rotation of the hand by abutment of the posterior of the hand there against in use; a third flexible strap secured to the wall, there being complementary hook and loop fasteners disposed on the outer back of the wall and the free end of the strap to permit the free end of the strap to be secured in place, wherein the third strap and fasteners therefor are disposed to permit securing of the strap in a position in which the strap is extended across a mid-anterior surface of the palm of the hand and through the bottom of the cleft located between the thumb and index finger so as to substantially, limit rotational movement of the hand located in a position in which the posterior is in abutment against the inner surface portion of the distal first end of the tubular member out of the position to about 20°; and a first end of the rigid member extends distally to abut the radiocarpal joint so as to cooperate with the inner surface portion of the tubular member to substantially hold the posterior portion of the forearm in place with respect to the tubular member while permitting movement of the fingers and thumb.

In another aspect of the invention, the wrist support comprises a central first vent defined in the wall to permit access of ambient air to a posterior portion of the person's forearm therethrough, in use, and the first strap is located distally of the second strap and the vent, in a position so as to traverse the radiocarpal joint.

In yet another aspect of the invention, the wrist support comprises a second strap, which is located proximally of the vent so as to traverse a portion of the forearm of the person, in use.

In yet another aspect of the invention, each strap of the wrist support is about one inch in width, the first and second straps are generally parallel to each other and each is in a plane generally perpendicular to a longitudinal axis of the tubular member.

In yet another aspect of the invention, the third strap of the wrist support is secured to the tubular member so as to be located adjacent the head knuckle of the baby finger of the person, in use.

In yet another aspect of the invention, the midlines of the first and second straps of the wrist support are axially spaced about two and one half inches from each other.

In yet another aspect of the invention, the wrist support comprises a hole defined the flared portion of the tubular member of the wrist support located to communicate with the bottom of the cleft in use and the third strap passes through the hole.

In yet another aspect of the invention, the concave surface of the flared portion of the tubular member of the wrist support forms an angle of up to about 30° with respect to the longitudinal axis.

In yet another aspect of the invention, the fasteners on the outer back of the wall of the wrist support for the third strap located in an axial position coincident with axial position of the fasteners on the outer back of the wall for at least one of the first and second straps, so as to necessitate and the at least one strap traverses the fasteners on the outer back of the wall for the third strap, so as to necessitate securing the third strap in place during installation of the wrist support prior to securing the at least one of the first and second straps.

In yet another aspect of the invention, the tubular member of the wrist support is comprised of plastic and a central spine area of the tubular member is thickened so as to substantially preclude flexure of the thickened area in any direction during use.

In yet another aspect of the invention, a second vent is defined in the wall located axially distally of the first vent to permit access of ambient air to a posterior portion of the hand, in use.

In yet another aspect of the invention, a third vent defined in the wall of the tubular member of the wrist support is located axially proximally of the first vent to permit access of ambient air to a posterior portion of the forearm, in use.

In yet another aspect of the invention, the proximal end of the tubular member of the wrist support is flared so as to provide clearance for a sleeve of the person in use.

In yet another aspect of the invention, the inner concave wall of the tubular member comprises a cushioning means on the inner concave wall of the tubular member Further, the cushioning means in the region between the first and second vents is wedge shaped with the widest portion of the wedge facing distally and tapering in thickness towards the proximal, lateral and medial aspects of the member.

BRIEF DESCRIPTION OF THE DRAWINGS

These and other features of the present invention will become more apparent upon reference to the drawings wherein:

FIGS. 8A–8D shows the range of movements permitted by the wrist support device of FIG. 1A and FIG. 1B.

DETAILED DESCRIPTION OF THE PREFERRED EMBODIMENT

With reference to the drawings, there is provided a wrist supporting device 10 to substantially limit movement about the wrist in all but a single direction and to substantially prevent pressure from being placed on the wrist. The support is intended to permit limited use of the hand, e.g., closing the fingers onto the handle of a hammer to permit use thereof while preventing damage or aggravating an already injured wrist joint.

Figure 1A:
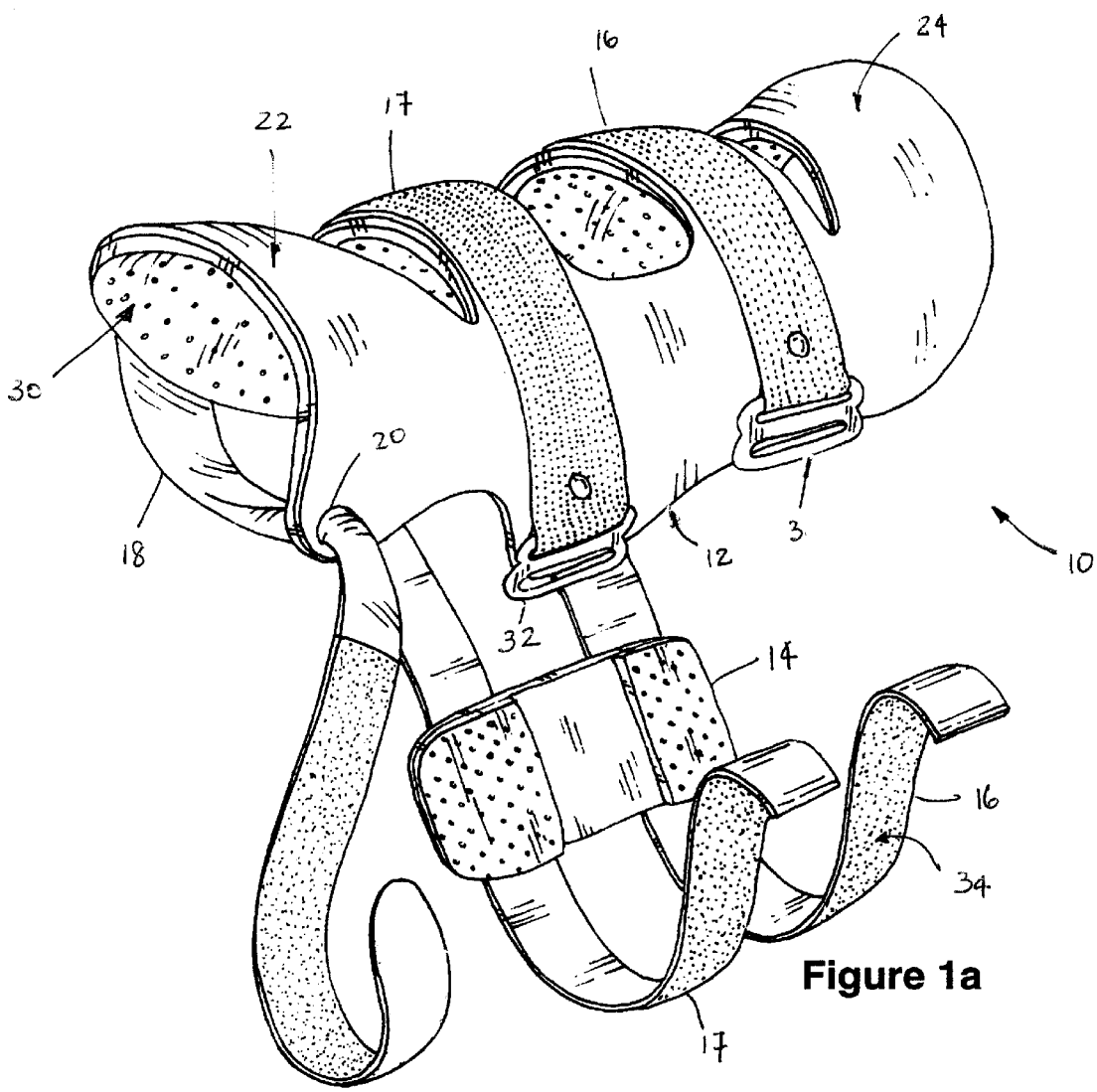
FIG. 1A is a perspective view of the wrist support device with the fastening members open.
Figure 1B:
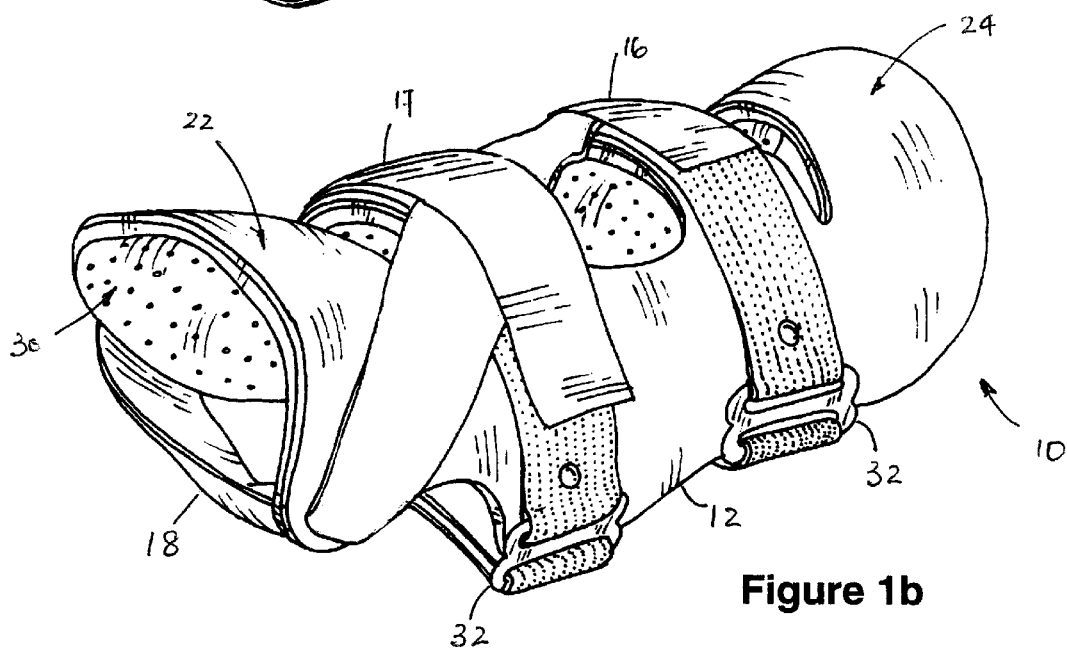
FIG. 1B is a perspective view of the wrist support device with the fastening members closed.
Figure 2:
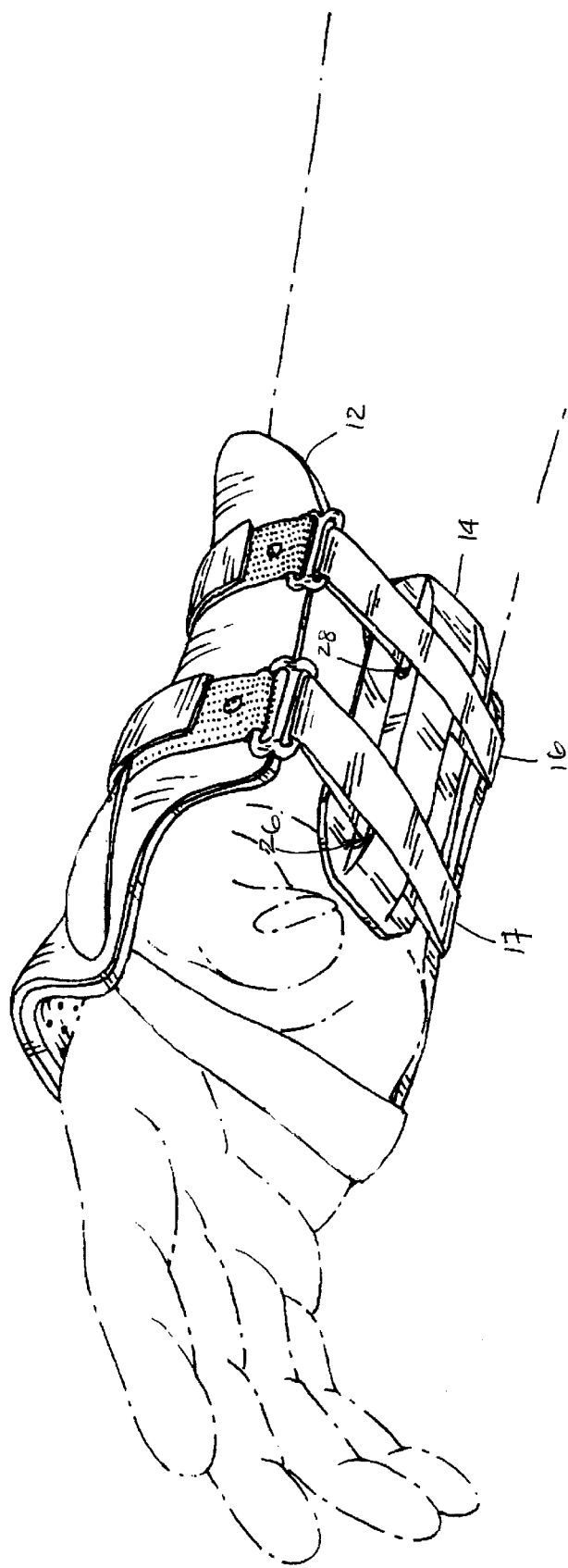
FIG. 2 is a view of the wrist support device attached to the forearm of a user viewed at an angle towards the thumb from underneath the hand.
Figure 3:
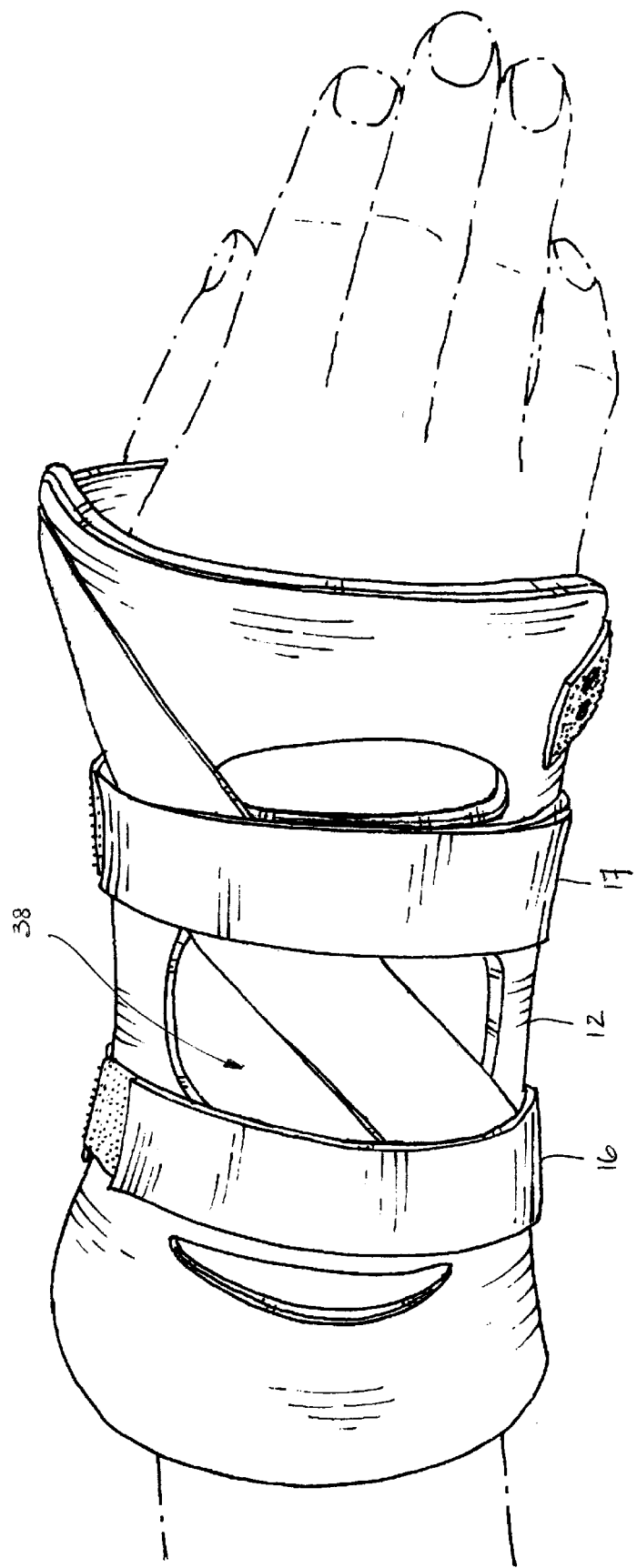
FIG. 3 is a top view of a hand and lower forearm wearing the wrist support device.
Figure 4:
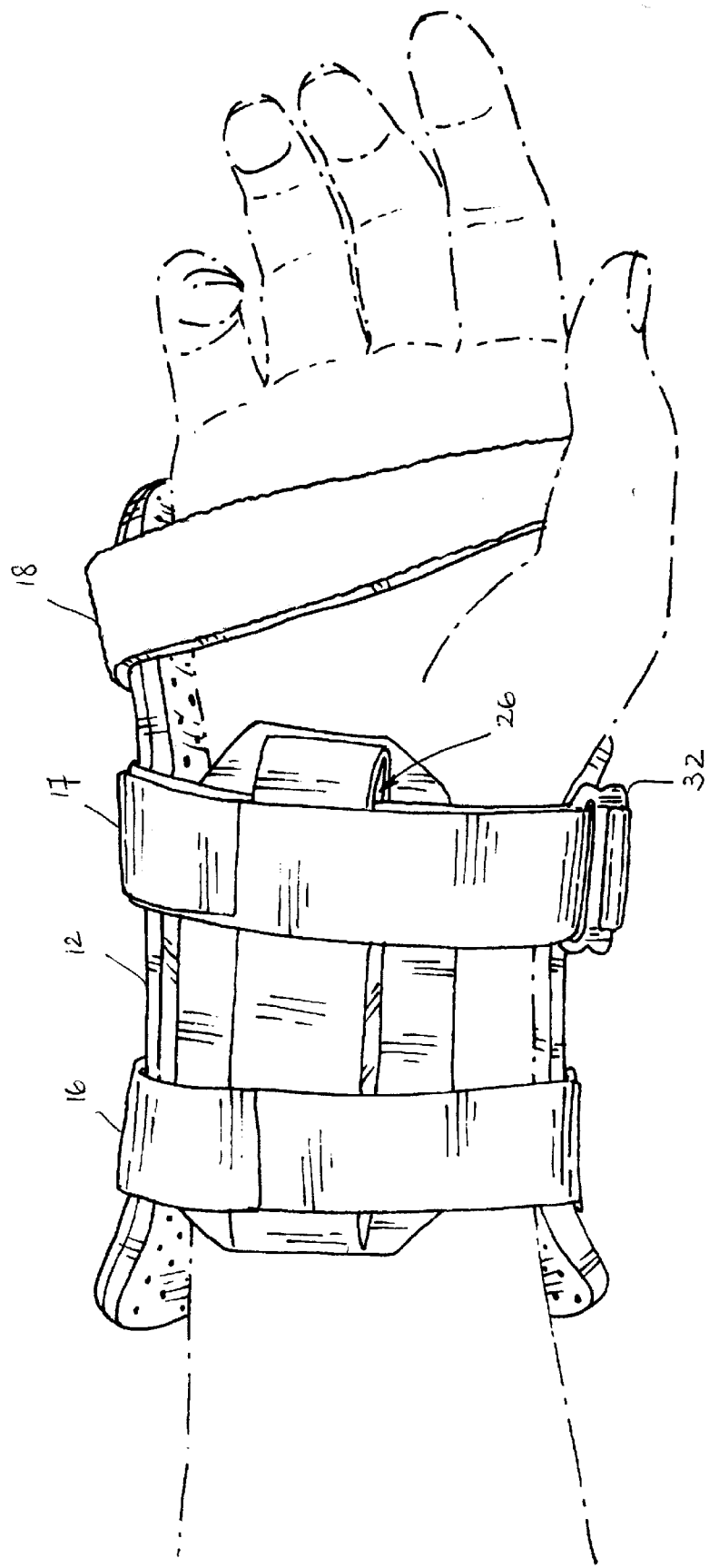
FIG. 4 is a view of a hand and lower forearm wearing the wrist support device with the palm side up.
Figure 5:
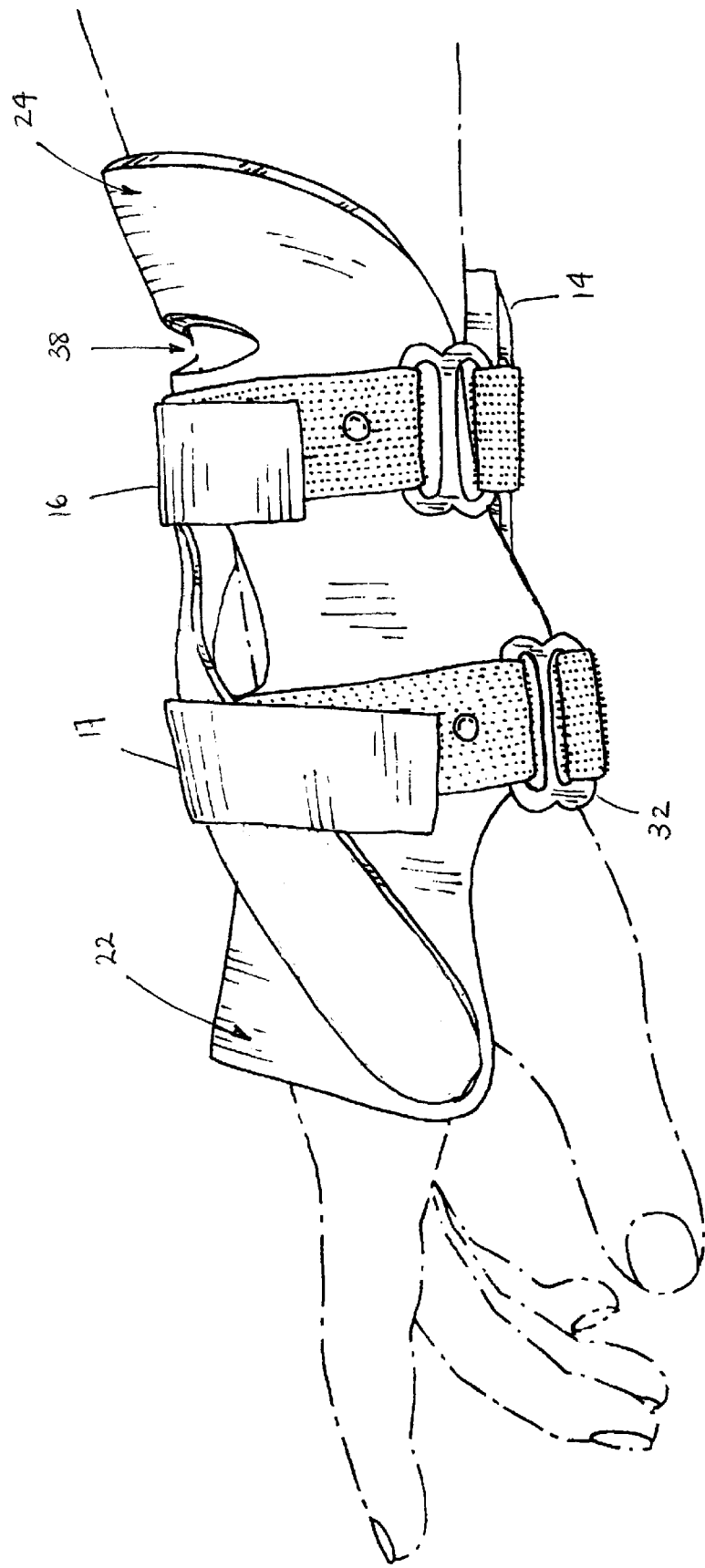
FIG. 5 is a lateral view of a hand and lower forearm wearing the wrist support device.
Figure 6:
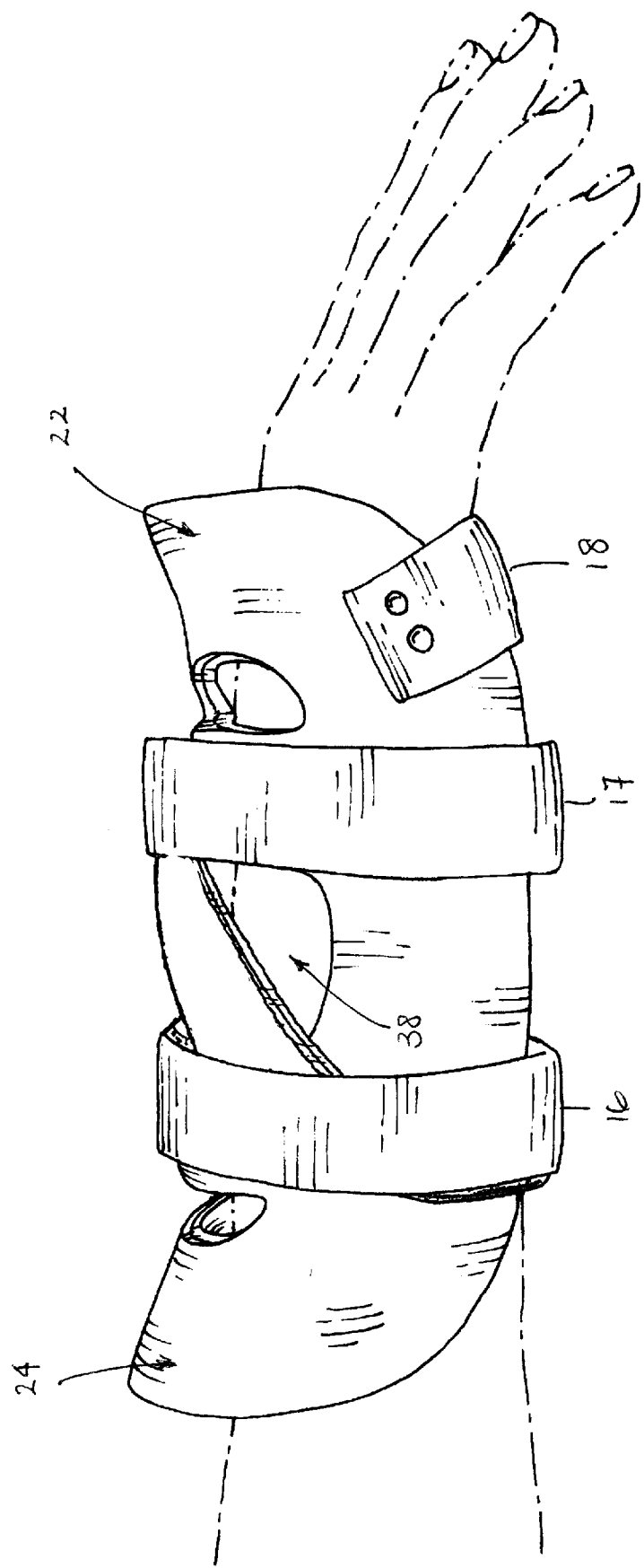
FIG. 6 is a medial view of a hand and lower forearm wearing the wrist support device.

The wrist supporting device 10 as shown in FIGS. 1A and 1B comprises a relatively rigid elongated channel shaped unitarily formed member 12 having a longitudinal axis 13 (FIGS. 7A and 7B), a small rigid substantially flat member 14, fastening members 16,17 for attaching together members 12 and 14 and retaining members 12 and 14 on the wearer's arm, and a strap 18 which is fixedly attached to the distal portion 22 of member 12 as seen in FIG. 6. The free end of strap 18, one side of which incorporates the pile layer of a Velcro strap, is passed through aperture 20. In this configuration, strap 18 spans the wearer's palm between the thumb and index finger as seen in FIGS. 2 and 4. It is preferable that the portion of strap 18 spanning the palm be made of leather. The lateral and medial aspects of member 12 are shaped such that they substantially surround the lateral and medial aspects of the wearer's forearm. Fastening members 16,17 which may be made of any suitable material are fixedly attached at one end to member 12, the free ends of fastening members 16,17 pass through two slots 26,28 (FIGS. 2 and 4) located at opposite ends of member 14 on its outer surface. In the embodiment shown in FIGS. 1–6, the fastening members 16,17 comprise Velcro™ straps, which are fixedly attached to member 12 and are aligned substantially parallel across the width of the members 12,14. Each of the Velcro straps 16,17 incorporates a pile layer 34 for part of the strap and a hook layer 36 for part of the strap. In the embodiment shown in FIGS. 1–6, the hook layer 36 is fixedly attached and encircles member 12 while the free ends of straps 16,17 incorporates the pile layer 34 and pass through slots 26,28 located on member 14. As is readily apparent, the hook and pile layers 34,36 of straps 16,17,18 may be reversed.

Preferably, members 12,14 of the wrist support device include a cushioning layer 30 on the inner surface of both members 12 and 14. The cushioning layer 30 increases the comfort to a user when wearing the device 10 and may also provide an impact absorbing benefit. The length of member 12 is such that when worn it extends from about the metacarpo-phalangeal joint at distal end 22, to about the mid forearm at proximal end 24. The length of member 14 is such that when worn it extends from the carpo-metacarpal joint at one end to the lower forearm at the opposite end. To further aid in the comfort of the wearer, member 12 contains vents 38 (FIGS. 3, 5, and 7B) for ventilation purposes. As shown in the embodiment in FIGS. 1–8, it is preferable that member 12 has at least three vents. The portions of member 12 between the vents are reinforced with either the same material comprising member 12 or with any other resilient member to maintain the shape of member 12 when straps 16,17 are tightened. It is important, however, that no vents correspond to the radiocarpal joint of the wearer, as this aids in the proper support and comfort of the wearer when flexing the hand. Further, for proper support and comfort of the wearer, the anterior surface of the portion of member 12 overlying the radiocarpal joint of the wearer should be wedge shaped with the widest part of the wedge facing distally and tapering in thickness towards the proximal, lateral and medial aspects of member 12.

When wearing wrist support device 10, strap 18 is first tightened and the pile layer at its free end is attached to the top of member 12 by interacting with the hook layer 36 of straps 16,17. Members 12,14 of the wrist support device 10 are next secured to the forearm, wrist and hand of the user by straps 16,17. The Velcro straps 16,17, each having a buckle 32 at one end, encircle the members 12,14, wrap through their respective buckles 32 and double back onto themselves. As straps 16,17 pass through their respective buckle 32 and are folded back on themselves, the pile layer 34 of each strap 16,17 interacts with the hook layer 36 of each strap 16,17 thereby fixing the straps 16,17 and members 12,14 in place. This arrangement of the fastening members 16,17 increases the strength of the hold of the straps 16,17 around the members 12,14 and allows for easy adjustment of the wrist support device 10 on the arm of a wearer.

Figure 7A:
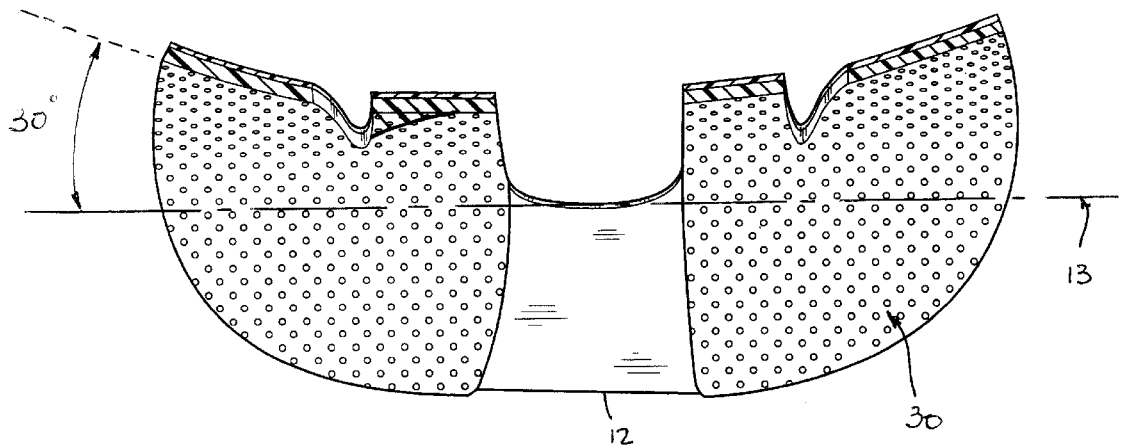
FIG. 7A is a sectional view of the wrist support device about the longitudinal axis.
Figure 7B:
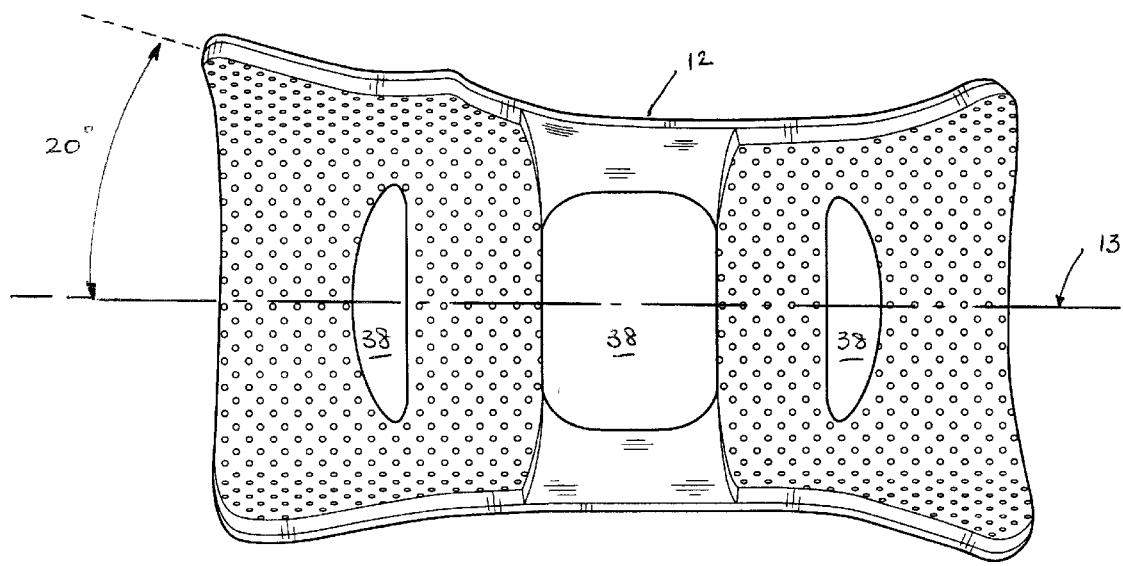
FIG. 7B is a view of the wrist support device from below.

The shape of member 12 is of particular importance in the way it limits movement about the wrist joint. A preferred feature of the wrist support device 10 is that the proximal and distal ends 24 and 22 of member 12 are curved upwards and outwards, i.e., flared, at a 30° and 20° angle respectively (FIGS. 7A and 7B). When wrist support device 10 is worn, member 12 extends from about the metacarpo-phalangeal joint to the mid forearm of the wearer's hand and member 14 extends from about the carpo-metacarpal joint to about the lower forearm of the wearer's hand.

Referring now to FIGS. 8A–8D pivotal movement about the wrist in the direction of arrow 40 in FIG. 8A is precluded by abutment of the person's arm and hand at points 42, 44, and 46. Likewise in FIG. 8B, pivotal movement about the wrist in the direction of arrow 48 is precluded by abutment of the person's arm and hand at points 50, 52, and 54. In FIG. 8C, extension of the wrist in the direction of arrow 56 is limited by abutment of the person's arm and hand at points 58, 60, and by the end of member 14 at the carpo-metacarpal joint (not shown in FIG. 8C). It will also be noted that forces normally exerted on the wrist by a person holding an object in their hand (with the hand in a position inverted to that shown in FIG. 8C) are transferred away from the wrist by the same abutments. FIG. 8D shows limited flexion in the direction of arrow 62 as a result of abutment at points 64 and 66 and by the end of member 14 at the lower forearm of the wearer (not shown in FIG. 8D). In addition, strap 18, which is not well illustrated in the drawing, by wrapping around the palm of the hand limits flexion of the wrist, but at the same time permits free movement of the fingers. This arrangement permits a wearer, for example, to readily grasp and use a tool such as a hammer or screwdriver. In fact, one use of this support might be by such a workman, since the action of hammering can be readily carried out by a wearer with reduced stress on the wrist.

The above described embodiments of the present invention are meant to be illustrative of preferred embodiments of the present invention and are not intended to limit the scope of the present invention. Various modifications, which would be readily apparent to one skilled in the art, are intended to be within the scope of the present invention. The only limitations to the scope of the present invention are set out in the following appended claims.

What is claimed is:

1. A wrist support device for allowing limited extension and flexion of the wrist but substantially limiting movement of the wrist in all other directions and further substantially limiting pressure from being placed on the wrist, the device comprising:

a first elongated channel shaped rigid member having a generally longitudinal axis for aligning with the longitudinal axis of a user's forearm and abutting against the posterior aspect of the forearm, wherein the lateral and medial aspects of the member substantially surround the lateral and medial aspects of the user's forearm, the member extending from about the metacarpophalangeal joint of the user's hand to about the mid forearm, the proximal and distal portions of the member curved upwards at about a 30° angle and curved outwards at about a 20° angle relative to the longitudinal axis, the distal edge portion of the member further having an aperture for receiving a strap having a first part of hook and loop fasteners disposed thereon, wherein one end of the strap is fixedly attached to the distal portion of the member substantially opposite the aperture and the free end of the strap is passed through the aperture for releasably attaching to the top surface of the member by means of a second part of the hook and loop fasteners disposed on the top surface, wherein the strap spans the wearer's palm between the thumb and the index finger;

a second small rigid substantially flat member independent from the first member for aligning with the longitudinal axis of the user's forearm and abutting against the anterior aspect of the forearm, the second member extending from about the carpo-metacarpal joint of the user's hand to about the lower forearm; and a plurality of releasably attaching fastening members adapted to attach the first and second members together and secure the first and second members to the wearer's hand such that when the fastening members are tightened the second member abuts the anterior aspect of the user's arm and is positioned so as to extend from about the carpo-metacarpal joint of the user's hand to about the lower forearm thereby limiting extension and flexion of the wrist and substantially limiting pressure being placed on the wrist.

2. The wrist support as claimed in claim 1, wherein the first member includes vents for providing comfort to the wearer such that none of the vents are positioned to correspond to the radio-carpal joint of the wearer's wrist.

3. The wrist support as claimed in claim 1 or 2, wherein the first and second members further comprise cushioning means on the surface abutting the wearer's arm for providing comfort to the wearer.

4. The wrist support as claimed in claim 3, wherein the portion of the strap spanning the wearer's palm between the thumb and index finger comprises leather.

5. The wrist support device of claim 3, wherein the cushioning means of the first member in the region corresponding to the radiocarpal joint is wedged shape with the widest portion of the wedge facing distally and tapering in thickness towards the proximal, lateral and medial aspects of the member.

6. The wrist support of claim 1, wherein the proximal portion of the member is curved upwards at about a 30° angle.

7. A wrist support to immobilize movement of the hand and forearm of a person with respect to each other about the wrist, the support comprising:

a tubular member comprising a wall of generally arcuate cross section, shaped to receive contiguous portions of a person's forearm, wrist and hand therein, wherein the member is dimensioned and is sufficiently flexible to permit radially inward flexure of the lengthwise sides of the member for fitting of the posterior and side surfaces of the forearm, wrist and hand in abutment against an inner concave surface of the wall in use, and sufficiently rigid to preclude flexure of the wall in other directions;

first and second flexible straps, wherein each strap is secured to the outer back of the wall and disposed to permit extension of the strap from a first lengthwise edge to a second lengthwise edge of the tubular member, to span a gap between the edges, wherein there is an aperture defined adjacent the second lengthwise edge to permit passage of the strap therethrough and looping of the strap back onto itself, to permit said radial inward flexure of the lengthwise sides of the member by drawing of the strap through the aperture;

complementary hook and loop fasteners disposed on the outer back of the wall and the free end of each strap to permit the looped-back end of each strap to be secured in a position selected by the person in which the inner concave surface of the wall is in abutment with the posterior and sides of the forearm, wrist and hand;

a rigid member having first and second openings therein for passage of the first and second straps therethrough to locate the rigid member in said gap, in use, in abutment with an anterior surface of the arm wherein:

each opening is dimensioned with respect to the strap passing therethrough such that the rigid member is substantially fixed against axial movement with respect to the tubular member when the straps are in a said secured position;

a distal first end of the tubular member is flared such that an inner surface portion thereof limits rotation of the hand by abutment of the posterior surfaces of the hand there against in use;

a third flexible strap secured to the wall, there being complementary hook and loop fasteners disposed on the outer back of the wall and the free end of the strap to permit the free end of the strap to be secured in place, wherein:

the third strap and fasteners therefor are disposed to permit securing of the strap in a position in which the strap is extended across a mid-anterior surface of the palm of the hand and through the bottom of the cleft located between the thumb and index finger so as to substantially, limit rotational movement of the hand located in a position in which the posterior is in said abutment against said inner surface portion of the distal first end of the tubular member out of said position to about 20°; and a first end of the rigid member extends distally to abut the radiocarpal joint so as to cooperate with said inner surface portion of the tubular member to substantially hold the posterior portion of the forearm in place with respect to the tubular member while permitting movement of the fingers and thumb.

8. The wrist support of claim 7, wherein there is a central first vent defined in the wall to permit access of ambient air to a posterior portion of the person's forearm therethrough, in use, and the first strap is located distally of the second strap and the vent, in a position so as to traverse the radiocarpal joint.

9. The wrist support of claim 8, wherein the second strap is located proximally of the vent so as to traverse a portion of the forearm of the person, in use.

10. The wrist support of claim 9, wherein each strap is about one inch in width, the first and second straps are generally parallel to each other and each is in a plane generally perpendicular to a longitudinal axis of the tubular member.

11. The wrist support of claim 10 wherein the third strap is secured to the tubular member so as to be located adjacent the head knuckle of the baby finger of the person, in use.

12. The wrist support of claim 11 wherein the midlines of the first and second straps are axially spaced about two and one half inches from each other.

13. The wrist support of claim 11 wherein there is a hole defined the flared portion of the tubular member located to communicate with said bottom of said cleft in use and the third strap passes through the hole.

14. The wrist support of claim 13 wherein the concave surface of the flared portion of the tubular member forms an angle of up to about 30° with respect to the longitudinal axis.

15. The wrist support of claim 14 wherein there are said fasteners on the outer back of the wall for the third strap are located in an axial position coincident with the fasteners on the outer back of the wall for at least one of the first and second straps, and the at least one strap traverses said fasteners on the outer back of the wall for the third strap, so as to necessitate securing the third strap in place during installation of the wrist support prior to securing the at least one of the first and second straps.

16. The wrist support of claim 15, wherein the tubular member is of plastic and a central spine area of the tubular member is thickened so as to substantially preclude flexure of the thickened area in any direction during use.

17. The wrist support of claim 16, wherein there is a second vent defined in the wall located axially distally of the first vent and to permit access of ambient air to a posterior portion of the hand, in use.

18. The wrist support of claim 17, wherein there is a third vent defined in the wall located axially proximally of the first vent and to permit access of ambient air to a posterior portion of the forearm, in use.

19. The wrist support of claim 18, wherein a proximal end of the tubular member is flared so as to provide clearance for a sleeve of the person in use.

20. The wrist support of claim 19, wherein the inner surface of the flared portion of the distal first end forms an angle of about 30° with the longitudinal axis of the tubular member.

21. The wrist support device of claim 17, further comprising a cushioning means on the inner concave wall of the tubular member, and wherein the cushioning means in the region between the first and second vents is wedge shaped with the widest portion of the wedge facing distally and tapering in thickness towards the proximal, lateral and medial aspects of the member.

* * * * *